Sept. 19, 1961 E. H. SCANLON Plant Pat. 2,092

LITTLELEAF LINDEN TREE

Filed Feb. 25, 1960 2 Sheets-Sheet 1

INVENTOR
EDWARD H SCANLON
BY Williams, Tilberry & Golrick
ATTORNEYS

LITTLELEAF LINDEN TREE

Filed Feb. 25, 1960 2 Sheets-Sheet 2

INVENTOR
EDWARD H SCANLON
By: Williams, Tilberry & Golrick
ATT'YS.

United States Patent Office

Plant Pat. 2,092
Patented Sept. 19, 1961

2,092
LITTLELEAF LINDEN TREE

Edward H. Scanlon, 7621 Lewis Road,
Olmsted Falls, Ohio

Filed Feb. 25, 1960, Ser. No. 11,116
1 Claim. (Cl. 47—59)

Figure 1:
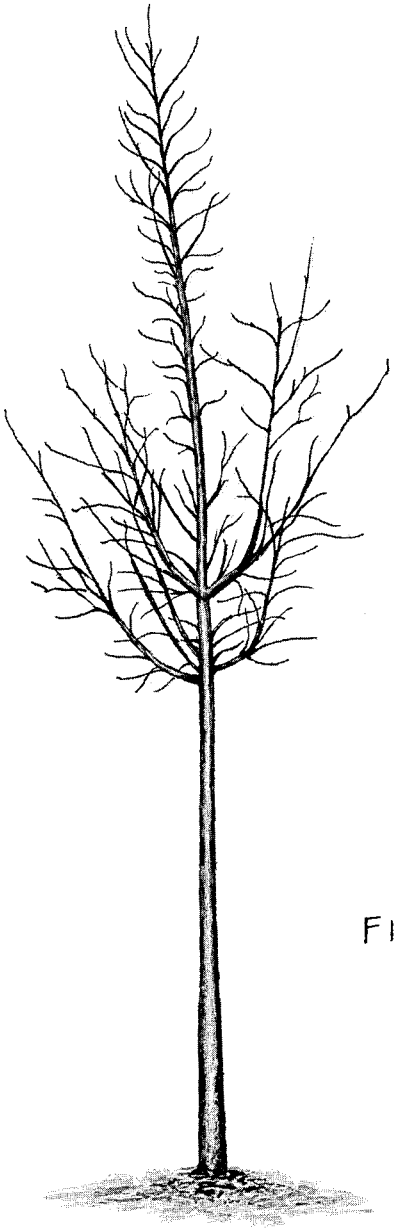

The present invention or discovery relates to a new and distinct variety of Littleleaf Linden tree (*Tilia cordata*).

This new variety was found among and selected from a group of some two thousand *Tilia cordata* seedlings planted in the applicant's nursery at Olmsted Falls, Ohio; and the selected seedling and over one thousand propagules, asexually reproduced therefrom and from others of said propagules by budding at Olmsted Falls, Ohio, consistently differed from the species in the characteristics hereinafter described.

Figure 2:
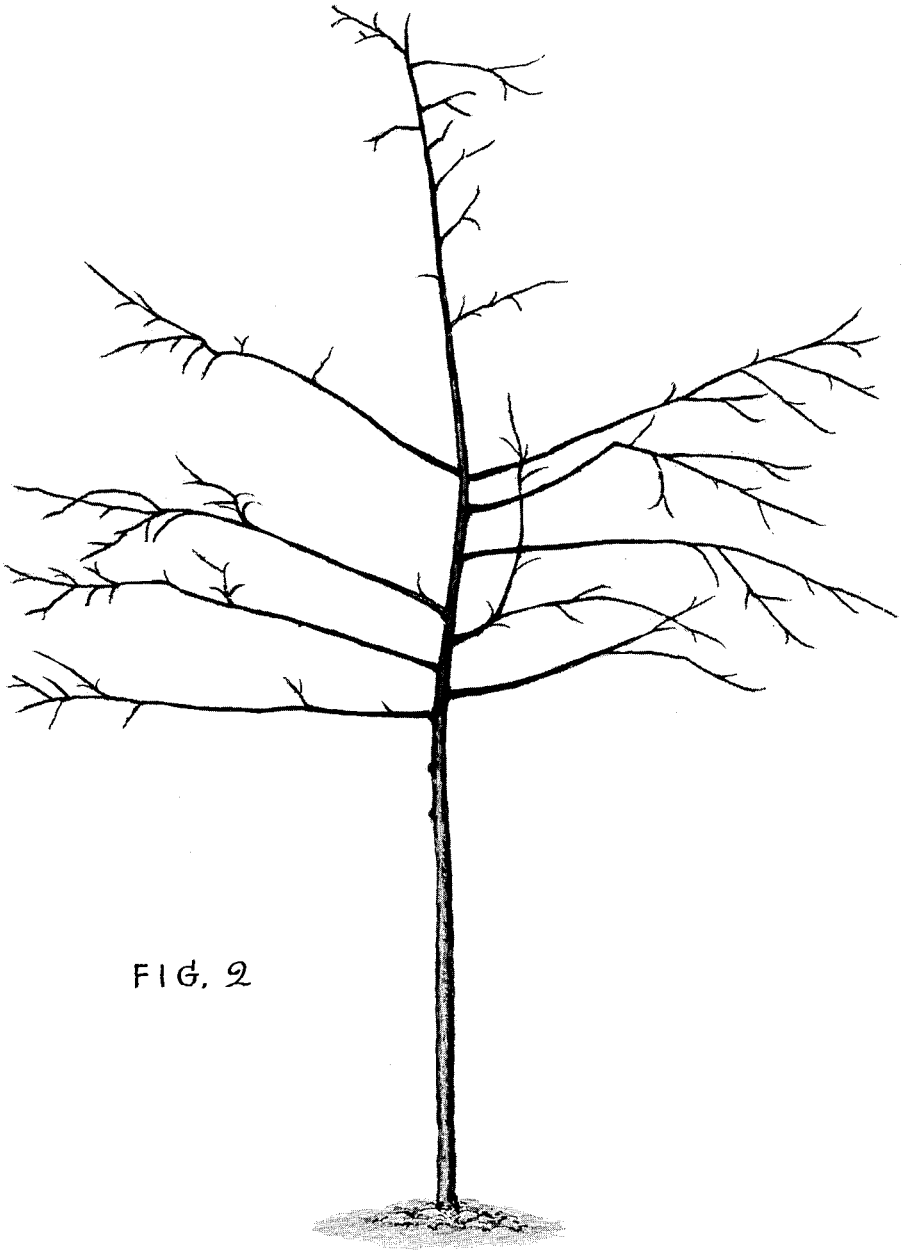

In the drawings,

FIG. 1 shows a tree of the instant variety of *Tilia cordata* in dormant state to present more clearly the straight growth and branching habit hereinafter described as distinguishing the same from the species; and FIG. 2 is a similar drawing of a young tree of normal *Tilia cordata* showing in contrast with FIG. 1 the rather crooked growth especially in the trunk and, for the eariler stage of growth, the fan-wise or flat branching habit, which are typical of the species.

Trees of the Littleleaf Linden species grow relatively slowly; and even in an early stage, the growth, particularly in the trunk, is twisted. Further in about the first eight years of growth to a marked degree the branching tends to be in opposite directions, fan-wise, that is the branching occurs predominantly in two opposite directions up the trunk. Eventually, in later years the tree branches out to fill in to a fair degree the spaces between the initial branching directions.

In contrast, the present new variety of Littleleaf Linden tree is characterized by its uniform branching habit and excurrent form; the branching occurring in whorls about the trunk, that is, in various directions along the length of the trunk to form a well-shaped crown, from the beginning of branching, as compared with the flat-type branching habit of the species. Further in comparison with the species, this new variety grows quite rapidly and straight.

Consequently, the variety presents a pleasing appearance from the time a crown is formed. Moreover, a marked uniformity in growth and shape has been found among propagules of like age and planting environment.

I claim:

A new and distinct variety of Littleleaf Linden tree (*Tilia cordata*), substantially as herein shown and described, characterized and distinguished from the species by its straight and rapid growth, its uniform branching habit in whorls about the trunk and its excurrent form.

No references cited.